United States Patent [19]
Beckmeyer et al.

[11] Patent Number: 5,156,834
[45] Date of Patent: Oct. 20, 1992

[54] ANTIPERSPIRANT COMPOSITIONS

[75] Inventors: Mary V. Beckmeyer; James A. Davis; Gary R. Kelm, all of Cincinnati, Ohio

[73] Assignee: The Procter & Gamble Company, Cincinnati, Ohio

[21] Appl. No.: 377,783

[22] Filed: Jul. 3, 1989

Related U.S. Application Data

[63] Continuation of Ser. No. 693,420, Jan. 22, 1985, abandoned, which is a continuation of Ser. No. 163,903, Jun. 30, 1980, abandoned, which is a continuation-in-part of Ser. No. 92,113, Nov. 7, 1979, abandoned.

[51] Int. Cl.$^5$ .................. A61K 7/32; A61K 7/34; A61K 7/36; A61K 7/38
[52] U.S. Cl. ........................ 424/47; 424/65; 424/66; 424/67; 424/68
[58] Field of Search ............... 424/65, 68, 47

[56] References Cited

U.S. PATENT DOCUMENTS

| | | | |
|---|---|---|---|
| 3,836,647 | 9/1974 | Lange | 424/184 |
| 3,903,258 | 9/1975 | Siegal | 424/66 |
| 4,053,581 | 10/1977 | Pader et al. | 424/68 |
| 4,054,670 | 10/1977 | Buhler | 424/358 |
| 4,065,564 | 12/1977 | Miles, Jr. et al. | 424/66 |
| 4,073,880 | 2/1978 | Pader | 424/66 |
| 4,083,956 | 4/1978 | Shelton | 424/66 |
| 4,122,029 | 10/1978 | Gee et al. | 252/309 |
| 4,126,679 | 11/1978 | Davy et al. | 424/66 |
| 4,151,272 | 4/1979 | Geary et al. | 424/68 |
| 4,152,416 | 5/1979 | Spitzer et al. | 424/68 |
| 4,174,386 | 11/1979 | Spitzer et al. | 424/47 |

FOREIGN PATENT DOCUMENTS 2018590 10/1979 United Kingdom ............... 424/47

OTHER PUBLICATIONS

Todd et al. Amer. Perf. Cosm., Oct. 1971.
Dow Corning New Product Bulletin Formulation E2-9031, Aug. 1973.
Todd et al., Cosmetics & Toiletries, Jan. 1976, vol. 91, pp. 29 to 32.
Drug & Cosmetic Industry, Nov. 1978, vol. I, p. 122.

Primary Examiner—Dale R. Ore
Attorney, Agent, or Firm—Douglas C. Mohl

[57] ABSTRACT

Antiperspirant compositions comprising a particulate antiperspirant material, a bulking/suspending agent, a volatile silicone and a non-volatile emollient.

9 Claims, No Drawings

ANTIPERSPIRANT COMPOSITIONS

CROSS REFERENCE TO RELATED APPLICATION

This is a continuation of application Ser. No. 693,420 filed on Jan. 22, 1985, now abandoned, which is a continuation of Ser. No. 163,903, filed Jun. 30, 1980, now abandoned, which is a continuation-in-part of our copending application Ser. No. 092,113, filed Nov. 7, 1979, now abandoned.

TECHNICAL FIELD

This invention relates to novel antiperspirant compositions which are useful in a variety of dispensing devices. The compositions comprise an antiperspirant material, a bulking/suspending agent, a volatile silicone and a non-volatile emollient.

BACKGROUND ART

The use of volatile silicones and non-volatile emollients in a variety of compositions has been suggested. References disclosing such compositions include U.S. Pat. Nos. 3,836,647, Sep. 17, 1974 to Lange; 3,903,258, Sep. 2, 1975 to Siegal, 4,053,581, Oct. 11, 1977 to Pader et al; 4,054,670, Oct. 18, 1977 to Buhler; 4,065,564, Dec. 27, 1977 to Miles, Jr. et al; 4,073,880, Feb. 14, 1978 to Pader et al; 4,083,956, Apr. 1, 1978 to Shelton; and 4,122,029, Oct. 24, 1978 to Gee et al.

Although the above-listed references describe a variety of compositions, they do not describe or suggest compositions similar to those of the present invention. Furthermore, the references do not suggest the surprising improvement in antiperspirant efficacy found with the present invention.

Accordingly, it is an object of the present invention to provide antiperspirant compositions having enhanced antiperspirant efficacy.

It is a further object of the present invention to provide antiperspirant compositions which are suitable for use in a number of dispensing devices.

DISCLOSURE OF THE INVENTION

The present invention relates to antiperspirant compositions comprising a particulate antiperspirant material, a bulking/suspending agent, a volatile silicone and a non-volatile emollient. The compositions are in the form of suspensions and are preferably anhydrous (containing less than about 1.5% water).

The particulate antiperspirant material comprises from about 10% to 70%, preferably from about 15% to 60%, by weight of the composition.

The bulking/suspending agent comprises from about 1% to 15%, preferably from about 2% to 8%, by weight of the composition.

The volatile silicone comprises from about 10% to 80%, preferably from about 15% to 70%, by weight of the composition.

The non-volatile emollient comprises from about 1% to 35%, preferably from about 5% to 30%, by weight of the composition.

DETAILED DESCRIPTION OF THE INVENTION

The necessary as well as optional components of the present compositions are described in detail below.

ANTIPERSPIRANT MATERIAL

The present compositions contain from about 10% to 70%, preferably 15% to 60%, by weight of a particulate antiperspirant material. Such materials include for example, many aluminum or zirconium astringent salts or complexes and are well known in the antiperspirant art.

Any aluminum astringent antiperspirant salt or aluminum and/or zirconium astringent complex in particulate form can be employed herein. Salts useful as astringent antiperspirant salts or as components of astringent complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y \cdot XH_2O$ where Q is chlorine, bromine or iodine; where x is 2 to 5 and $x+y=6$ and x and y do not need to be integers; and where X is about 1 to 6. Aluminum salts of this type can be prepared in the manner described more fully in Gilman, U.S. Pat. No. 3,887,692, issued Jun. 3, 1975, and U.S. Pat. No. 3,904,741, Sep. 9, 1975 to Jones and Rubino incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to 2 and need not be an integer, n is the valence of B, 2-nz is greater than or equal to 0, and B may be selected form the group consisting of halides, nitrate, sulfamate, sulfate and mixtures thereof. Although only zirconium compounds are exemplified in this specification, it will be understood that other Group IV B metals, including hafnium could be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example Luedders et al; U.S. Pat. No. 3,792,068, issued Feb. 12, 1974 discloses complexes of aluminum, zirconium and amino acids such as glycine. Complexes such as those disclosed in this Luedders et al '068 patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to 12.5 and a Metal:Cl ratio of from about 0.73 to 1.93.

Preferred ZAG complexes are formed by
(A) Co-dissolving in water
  (1) one part $Al_2(OH)_{6-m}Q_m$, wherein Q is an anion selected from the group consisting of chloride, bromide and iodide and m is a number from about 0.8 to about 2.0;
  (2) x parts $ZrO(OH)_{2-a}Q_a \cdot nH_2O$ where Q is chloride, bromide or iodide; where a is from 1 to 2; where n is from 1 to 8; and where x has a value of from about 0.16 to about 1.2;
  (3) p parts neutral amino acid selected from the group consisting of glycine, dl-tryptophane, dl-β-phenylalanine, dl-valine, dl-methionine and β-alanine, and where p has a value of from about 0.06 to about 0.53;
(B) Co-drying the resultant mixture to a friable solid; and
(C) Reducing the resultant dried inorganic-organic antiperspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from 1.5 to 1.87 and n is from about 1 to 7. The preferred amino acid for preparing such ZAG-type complexes is glycine of the formula $CH_2(NH_2)COOH$. Salts of such amino acids can also be employed in such antiperspirant complexes. See U.S. Pat. No. 4,017,599 to A. M. Rubino issued Apr. 12, 1977 specifically incorporated herein by reference.

A wide variety of other types of antiperspirant complexes are also known in the art. For example, Siegal; U.S. Pat. No. 3,903,258, issued Sep. 2, 1975 discloses a zirconium aluminum complex prepared by reacting zirconyl chloride with aluminum hydroxide and aluminum chlorhydroxide. Rubino; U.S. Pat. No. 3,979,510, issued Sep. 7, 1976 discloses an antiperspirant complex formed from certain aluminum compounds, certain zirconium compounds and certain complex aluminum buffers. Rubino; U.S. Pat. No. 3,981,896, issued Sep. 21, 1976 discloses an antiperspirant complex prepared from an aluminum polyol compound, a zirconium compound and an organic buffer. Mecca; U.S. Pat. No. 3,970,748, issued Jul. 20, 1976 discloses an aluminum chlorhydroxy glycinate complex of the approximate general formula $[Al_2(OHhd)Cl][H_2CNH_2COOH]$. All of these patents are incorporated herein by reference.

Of all the above types of antiperspirant actives, preferred compounds include the 5/6 basic aluminum salts of the empirical formula $Al_2(OH)_5Cl \cdot 2H_2O$; mixtures of $AlCl_3 \cdot 6H_2O$ and $Al_2(OH)_5Cl \cdot 2H_2O$ with aluminum chloride to aluminum hydroxychloride weight ratios of up to about 0.5; ZAG type complexes wherein the zirconium salt is $ZrO(OH)Cl \cdot 3H_2O$; the aluminum salt is $Al_2(OH)_5Cl \cdot 2H_2O$ or the aforementioned mixtures of $AlCl_3 \cdot 6H_2O$ and $Al_2(OH)_5Cl \cdot 2H_2O$ wherein the total metal to chloride molar ratio in the complex is less than about 1.25 and the Al:Zr molar ratio is about 3.3; and the amino acid is glycine and ZAG-type complexes wherein the zirconium salt is $ZrO(OH)_{2-a}Cl_a \cdot nH_2O$ with a ranging from about 1.5 to 1.87 and n ranging from about 1 to 7; the aluminum salt is $Al_2(OH)_5Cl \cdot 2H_2O$; and the amino acid is glycine.

As indicated previously the present compositions contain from about 10% to 70%, preferably from about 15% to 60%, by weight of the particulate astringent antiperspirant materials calculated on an anhydrous metal salt basis (exclusive of glycine, the salts of glycine or other complexing agents). Such particulate antiperspirant material is preferably impalpable, i.e. has particle sizes ranging from about 1 to about 100 microns, more preferably from about 1 to about 50 microns.

BULKING AGENT

Another essential component of the present compositions is a bulking or suspending agent. Such an agent is present at a level of from about 1% to 15%, preferably 2% to 8%.

Clays and colloidal pyrogenic silica pigments are the preferred materials for use as bulking/suspending agents. Colloidal silica is available commercially as Cab-O-Sil ®, a submicroscopic particulated pyrogenic silica.

Clay bulking/suspending agents suitable for use in the compositions of the present invention are selected from the group consisting of montmorillonite clays and hydrophobically treated montmorillonite clays. Montmorillonite clays are those which contain the mineral montmorillonite and are characterized by having a suspending lattice. Examples of these clays include the bentonites, hectorites, and colloidal magnesium aluminum silicates.

Bentonite is colloidal, hydrated aluminum slicate obtained from montmorillonite and has the formula $Al_2O_3 4SiO_2 \cdot H_2O$. A more detailed discussion of bentonites can be found in the KIRK-OTHMER ENCYCLOPEDIA OF CHEMICAL TECHNOLOGY, 2nd. ed., Vol 3(1964), pp. 339–360, published by Interscience Publishers, which is incorporated herein by reference. Hectorite, also a montmorillonite clay, differs from bentonite in that there is almost a complete substitution of aluminum in the lattice structure of bentonite by magnesium. In addition, hectorites contain lithium and fluorine Laponite is an example of a commercially available synthetic hectorite marketed by Laporte, Industries, Ltd.

The magnesium aluminum silicates are complexes of colloidal magnesium aluminum silicate richer in magnesium than aluminum. Magnesium aluminum silicates are commercially available as Veegum (R. T. Vanderbilt Co.).

Preferred clay suspending agents for use in the present invention are certain hydrophobically treated montmorillonite clays, e.g., hydrophobic bentonites available under the tradename of "Bentone". Bentone is prepared by reacting bentonite in a cation exchange system with an amine. Different amines are reacted to obtain a variety of Bentones, which may also differ in proportions of $SiO_2$, $MgO$ and $Al_2O_4$. Specific examples of Bentones within the scope of the present invention are Bentone 38, Bentone 34, Bentone 27, Bentone 14, and Bentone LT, all of which have a particle size of below about 5 microns and are commercially available from the NL Industries, Inc.

VOLATILE SILICONE

The volatile silicone component of the present invention can be either a cyclic or a linear polydimethylsiloxane and is present at a level of from about 10% to 80%, preferably 15% to 70%.

The cyclic silicones preferably have 3 to 6 silicon atoms, more preferably 5.

The general formula for such silicones is

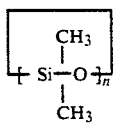

wherein n = 3-6

The linear polydimethylsiloxanes have from about 3 to 9 silicon atoms and have the general formula

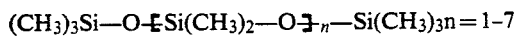

Silicones of the above type are offered by Dow Corning Corporation, Dow Corning 344, 345 and 200 fluids, Union Carbide, Silicone 7207 and Silicone 7158, and Stauffer Chemical, SWS-03314.

The linear volatile materials generally have viscosities of less than about 5 centistokes at 25° C. while the cyclic materials have viscosities less than about 10 centistokes. "Volatile" means that the material has a measurable vapor pressure. A description of volatile silicones is found in Todd and Byers, "Volatile Silicone Fluids for Cosmetics", *Cosmetics and Toiletries*, Vol. 91, January, 1976, pp. 27-32, incorporated herein by reference.

NON-VOLATILE EMOLLIENT

The non-volatile emollient used in the present compositions can be either a non-volatile silicone or liquid paraffin material such as mineral oil. Such materials have a viscosity of from about 5 centistokes to 2,500,000, preferably from about 10 to 100,000 centistokes at 25° C.

The non-volatile silicone fluid may be either a polyalkyl siloxane, a polyalkylaryl siloxane or a polyether siloxane copolymer.

The essentially non-volatile polyalkyl siloxanes that may be used include, for example, polydimethyl siloxanes with viscosities ranging from about 5 to 100,000 centistokes at 25° C. These siloxanes are available, for example, from the General Electric Company as the Vicasil series and from Dow Corning as the Dow Corning 200 series.

The essentially non-volatile polyalkylaryl siloxanes that may be used include, for example, polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid.

The essentially non-volatile polyether siloxane copolymer that may be used is, for example, a dimethyl polyoxyalkylene ether copolymer fluid having a nominal viscosity of about 1200 to 1500 centistokes at 25° C. This copolymer is available, for example, from the General Electric Company as SF-1066 organosilicone surfactant. Preferred compounds of this type are polysiloxane ethylene glycol ether copolymers.

In the present compositions, a ratio of nonvolatile emollient to suspending agent of less than about 10:1 is preferred when the suspending agent is a silica. The preferred ratio is less than about 2:1 when the suspending agent is a clay.

OPTIONAL COMPONENTS

The optional components which may be used with the present compositions vary with the type of dispenser used.

If the dispenser of choice is an aerosol, the present compositions are combined with an aerosol propellant and perhaps a material to serve as carrier liquid The propellant gas can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, butane and isobutane, used singly or admixed. Isobutane, used singly or admixed with other hydrocarbons, is preferred.

The amount of the propellant gas is governed by normal factors as well known in the aerosol art. The composition described previously herein serves as the concentrate and comprises from about 7% to about 45%, preferably 20% to about 40%, of the present total aerosol composition while the propellant comprises from about 55% to about 93%, preferably from about 60% to about 80%.

If a propellant such as dimethylether utilizes a vapor pressure suppressant (e.g: trichloroethane or dichloromethane) the amount of suppressant is included as part of the propellant.

Although the nonvolatile silicone or mineral oil may suitably serve as a carrier liquid in aerosols additional materials may also be used. The carrier liquid aids efficacy by keeping the antiperspirant compound in contact with the skin so that it does not flake off or wash off. Examples of additional materials are carboxylic esters like isopropyl myristate and isopropyl palmitate; alcohols such as lauryl alcohol, hexadecyl alcohol, and oleyl alcohol; carboxylic acids such as lauric and oleic acid; and lanolin and its derivatives such as acetylated lanolin. Other operable carrier liquids are more hydrophilic than the above-mentioned compounds, for example, organic compounds containing multiple ester groups. This includes, but it not limited to, diesters of dibasic organic acids. Examples of compounds containing multiple ester groups that are suitable for the instant invention are di-n-butyl phthalate, diethyl sebacate, diisopropyl adipate, and ethyl ethylcarbomethyl phthalate [ortho $C_2H_5OOC-\phi-COOCH_2COOC_3H_5$].

Still other operable carrier liquids are even more hydrophilic than these esters. Among them are polyethylene glycol monolaurate and butoxy-polyoxyethylene oxypropylene glycols (the Ucon 50 HB series; trade mark Union Carbide).

Among these various carrier liquids, carboxylic esters having from about 12 to about 16 carbon atoms are preferred. As described supra, they can be either aliphatic or aromatic and can contain either one ester group or multiple ester groups. Especially preferred are di-n-butyl phthalate, diethyl sebacate, diisopropyl adipate, isopropyl myristate and ethyl ethylcarbomethyl phthalate.

Any of the additional carrier liquids described supra can be used in amounts from about 1% to about 15% of the total aerosol composition.

The present compositions in aerosol form may also contain low levels of high molecular weight polymers similar to those described in U.S. Pat. No. 4,152,416, May 1, 1979 to Spitzer et al. These polymeric materials are used at a level of from about 0.005% to 5% of the total aerosol composition. A preferred material is polyvinylisobutyl ether.

Another optional material in aerosol compositions is a polar material such as ethanol or propylene carbonate at a level of from about 0.25% to 5% of the total aerosol composition.

If the present composition is used in a roll-on dispenser, a component such as ethanol may be present in an amount from about 7% to 18%.

Regardless of the dispensing device employed, additional components such as perfumes, antimicrobials, fillers (e.g. talc) etc. may be included in the compositions. If present these components comprise from about 0.002% to 10.0% of the total compositions

METHOD OF MANUFACTURE

The compositions of the present invention are prepared by simply mixing together in any order and by conventional means known in the art the essential and optional components herein.

COMPOSITION USE

The present antiperspirant compositions are used in conventional manner.

Following are non-limiting examples of the present invention. All percentages in the examples and elsewhere herein are by weight unless otherwise specified.

EXAMPLE I

A composition of the present invention having the following composition was formulated.

| | |
|---|---|
| Cyclomethicone[1] | 58.20% |
| Cab-o-Sil HS-5[2] (fumed silica) | 3.50 |
| ZAG[3] | 26.70 |
| Dimethicone[4] 350 Centistoke Viscosity at 25° C. | 11.60 |
| | 100.00% |

[1] Volatile cyclic silicone having 5 silicon atoms offered by Union Carbide Corporation - Silicone 7158.
[2] Cabot Corporation
[3] Complex of zirconyl hydroxychloride as taught in U.S. Pat. No. 3,792,068. February 12. 1974 to Luedders et al.
[4] Non-volatile polydimethyl silicone offered by Dow Corning - Dow Corning 200.

The above composition is used in a dispenser such as that described in U.S. Pat. No. 4,167,245, Sep. 11, 1979 and is a very effective antiperspirant.

When Cab-o-Sil HS-5 is replaced by a Bentone a composition having similar improved efficacy is achieved. Similarly the cyclomethicone may be replaced by another volatile silicone and the dimethicone may be replaced by another nonvolatile silicone or a mineral oil.

EXAMPLE II

A second composition of the present invention has the following formula

| | |
|---|---|
| Cyclomethicone | 35.9% |
| Cab-o-Sil HS-5 | 3.5 |
| ZAG | 26.7 |
| Mineral oil having a viscosity of 21 centistokes at 25° C. | 33.9 |
| | 100.00% |

The above composition is used in a dispenser as referred to in Example I.

EXAMPLE III

A third composition of the present invention is as follows

| | |
|---|---|
| Cyclomethicone | 7.000% |
| Bentone 38 | 1.250 |
| Isopropyl Myristate | 7.145 |
| Propylene Carbonate | 0.400 |
| Aluminum chlorohydroxide ($Al_2(OH)_5Cl.2H_2O$) | 12.000 |
| Ethylene Brassylate | 0.005 |
| Dimethicone 60,000 centistoke viscosity at 25° C. | 3.000 |
| Isobutane | 69.200 |
| | 100.000% |

The above composition is used in a conventional aerosol container.

What is claimed is:

1. An antiperspirant composition comprising:
   (a) from about 10% to 70% of a particulate antiperspirant material;
   (b) from about 1% to 15% of a bulking/suspending agent;
   (c) from about 10% to 80% of a volatile silicone agent; and
   (d) from about 1% to 35% of a nonvolatile silicone emollient.

2. An antiperspirant composition in accordance with claim 1 wherein the bulking/suspending agent is selected from the group consisting of clays and colloidal pyrogenic silica pigments and mixtures thereof.

3. An antiperspirant composition in accordance with claim 2 wherein the particulate antiperspirant material is a zirconium aluminum complex.

4. An antiperspirant composition in accordance with claim 3 wherein the amount of particulate antiperspirant material is from about 15% to 60%, the amount of bulking/suspending agent is from about 2% to 8%, the amount of volatile silicone is from about 15% to 70% and the amount of non-volatile emollient is from about 5% to 30%.

5. An antiperspirant composition in accordance with claim 4 wherein the volatile silicone is cyclic.

6. An antiperspirant composition in accordance with claim 6 wherein the particulate antiperspirant material is an aluminum zirconium glycine complex.

7. An antiperspirant composition in accordance with claim 6 wherein the non-volatile emollient is a polydimethyl siloxane having a viscosity of from about 5 to 100,000 centistokes at 25° C.

8. An aerosol antiperspirant composition comprising from about 7% to 45% of a composition in accordance with claim 2 and from about 55% to 93% of an aerosol propellant.

9. An aerosol antiperspirant composition in accordance with claim 8 wherein the antiperspirant material is an aluminum salt.

* * * * *